(12) United States Patent
Niedbala et al.

(10) Patent No.: US 8,673,239 B2
(45) Date of Patent: Mar. 18, 2014

(54) SAMPLE COLLECTOR AND TEST DEVICE

(75) Inventors: R. Sam Niedbala, Allentown, PA (US); John W. Scott, Perkasie, PA (US); Peter A. Bourdelle, Allentown, PA (US); Hans H. Feindt, Allentown, PA (US)

(73) Assignee: Orasure Technologies, Inc., Bethlehem, PA (US)

( * ) Notice: Subject to any disclaimer, the term of this patent is extended or adjusted under 35 U.S.C. 154(b) by 207 days.

(21) Appl. No.: 13/017,324

(22) Filed: Jan. 31, 2011

(65) Prior Publication Data
US 2011/0120236 A1  May 26, 2011

Related U.S. Application Data

(63) Continuation of application No. 09/997,023, filed on Nov. 30, 2001, now Pat. No. 7,879,293.

(60) Provisional application No. 60/325,170, filed on Sep. 28, 2001.

(51) Int. Cl.
*G01N 33/48* (2006.01)
(52) U.S. Cl.
USPC ............ 422/501; 422/430; 422/535; 436/165
(58) Field of Classification Search
USPC ........................ 422/430, 501, 535; 436/165
See application file for complete search history.

(56) References Cited

U.S. PATENT DOCUMENTS

| | | | |
|---|---|---|---|
| 3,713,775 A | 1/1973 | Schmitz | |
| 4,014,322 A | 3/1977 | Shah | |
| 4,036,064 A | 7/1977 | Hydo | |
| 4,418,702 A | 12/1983 | Brown et al. | |
| 4,580,577 A | 4/1986 | O'Brien et al. | |
| 4,596,157 A | 6/1986 | Laauwe | |
| 4,750,373 A | 6/1988 | Shapiro | |
| D296,926 S | 7/1988 | Heasley | |

(Continued)

FOREIGN PATENT DOCUMENTS

| | | |
|---|---|---|
| WO | Wo 98/14276 | 4/1998 |
| WO | WO 01/49820 | 7/2001 |

OTHER PUBLICATIONS

International Search Report dated Dec. 27, 2002.

*Primary Examiner* — Lyle Alexander
(74) *Attorney, Agent, or Firm* — J.A. Lindeman & Co., PLLC

(57) ABSTRACT

A sample collector and test device is disclosed. The sample collector and test device may be used together as a diagnostic tool for collecting and assay of analytes contained in a sample. A sample collector is also disclosed which may be used with existing sample containers and or test devices. The sample collector may indicate sample adequacy when a sufficient volume of sample has been collected for assay and may also include a sample retaining feature which retains a portion of expressed sample for confirmatory testing, if desirable. The sample collector may also include a mechanism for expressing sample in a sample collector and/or test device. A test device is also disclosed for retaining and assay of an expressed sample. The disclosed test device may be used with existing sample collectors. In a preferred embodiment, test device is used with a preferred sample collector. Test device may include a locking feature for locking a sample retained on a sample collector or test device may be used to receive expressed sample collected from a syringe or another suitable sample delivery device.

8 Claims, 8 Drawing Sheets

(56) References Cited

U.S. PATENT DOCUMENTS

| | | |
|---|---|---|
| D299,859 S | 2/1989 | Fan et al. |
| D299,860 S | 2/1989 | Fan et al. |
| 4,857,453 A | 8/1989 | Ullman et al. |
| 4,895,808 A | 1/1990 | Romer |
| 4,943,522 A | 7/1990 | Eisinger et al. |
| 4,963,325 A | 10/1990 | Lennon et al. |
| 4,980,298 A | 12/1990 | Blake et al. |
| 4,981,786 A | 1/1991 | Dafforn et al. |
| 5,017,342 A | 5/1991 | Haberzettl et al. |
| 5,051,237 A | 9/1991 | Grenner et al. |
| D324,426 S | 3/1992 | Fan et al. |
| D328,135 S | 7/1992 | Fan et al. |
| 5,137,808 A | 8/1992 | Ullman et al. |
| 5,160,704 A | 11/1992 | Schluter |
| 5,198,193 A | 3/1993 | Bunce et al. |
| 5,211,182 A | 5/1993 | Deutsch et al. |
| 5,256,372 A | 10/1993 | Brooks et al. |
| 5,260,031 A | 11/1993 | Seymour |
| 5,260,222 A | 11/1993 | Patel et al. |
| D342,575 S | 12/1993 | Ashihara et al. |
| 5,268,148 A | 12/1993 | Seymour |
| 5,356,782 A | 10/1994 | Moorman et al. |
| 5,356,785 A | 10/1994 | McMahon et al. |
| 5,364,596 A | 11/1994 | Magnussen et al. |
| 5,376,337 A | 12/1994 | Seymour |
| 5,380,492 A | 1/1995 | Seymour |
| 5,384,264 A | 1/1995 | Chen et al. |
| 5,393,496 A | 2/1995 | Seymour |
| 5,494,646 A | 2/1996 | Seymour |
| 5,504,013 A | 4/1996 | Senior |
| 5,602,040 A | 2/1997 | May et al. |
| 5,609,160 A | 3/1997 | Bahl et al. |
| 5,622,871 A | 4/1997 | May et al. |
| 5,656,502 A | 8/1997 | MacKay et al. |
| 5,656,503 A | 8/1997 | May et al. |
| 5,714,389 A | 2/1998 | Charlton et al. |
| 5,739,041 A | 4/1998 | Nazareth et al. |
| 5,785,044 A | 7/1998 | Meador et al. |
| 5,792,424 A | 8/1998 | Homberg et al. |
| 5,821,073 A | 10/1998 | Lee |
| 5,824,268 A | 10/1998 | Bernstein et al. |
| 5,830,410 A | 11/1998 | Thieme et al. |
| D405,539 S | 2/1999 | Poissant et al. |
| 5,900,379 A | 5/1999 | Noda et al. |
| 5,910,122 A | 6/1999 | D'Angelo |
| 5,922,614 A | 7/1999 | Cesarczyk |
| 5,939,331 A | 8/1999 | Burd et al. |
| 5,962,336 A | 10/1999 | Sun |
| 5,965,453 A | 10/1999 | Skiffington et al. |
| 5,968,746 A | 10/1999 | Schneider |
| 5,976,895 A | 11/1999 | Cipkowski |
| 5,981,293 A | 11/1999 | Charlton |
| 5,989,921 A | 11/1999 | Charlton et al. |
| 6,027,943 A | 2/2000 | Kang et al. |
| 6,046,057 A | 4/2000 | Nazareth et al. |
| D427,314 S | 6/2000 | Herbst et al. |
| D431,867 S | 10/2000 | Maynard et al. |
| D432,244 S | 10/2000 | Anderson et al. |
| 6,140,136 A | 10/2000 | Lee |
| 6,146,590 A | 11/2000 | Mazurek et al. |
| 6,156,271 A | 12/2000 | May |
| 6,176,836 B1 | 1/2001 | Trudil et al. |
| 6,187,269 B1 | 2/2001 | Lancesseur et al. |
| 6,187,598 B1 | 2/2001 | May et al. |
| D438,632 S | 3/2001 | Miller |
| D438,633 S | 3/2001 | Miller |
| 6,267,722 B1 | 7/2001 | Anderaon et al. |
| 6,663,831 B2 | 12/2003 | Konecke |
| 7,114,403 B2 | 10/2006 | Wu et al. |
| 7,282,181 B2 * | 10/2007 | Hudak et al. .................. 422/549 |
| 7,879,293 B2 | 2/2011 | Niedbala et al. |

* cited by examiner

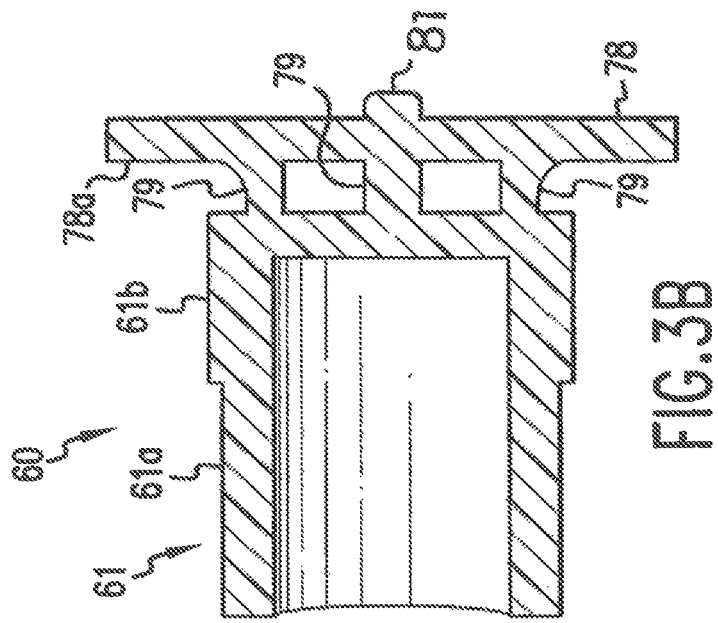
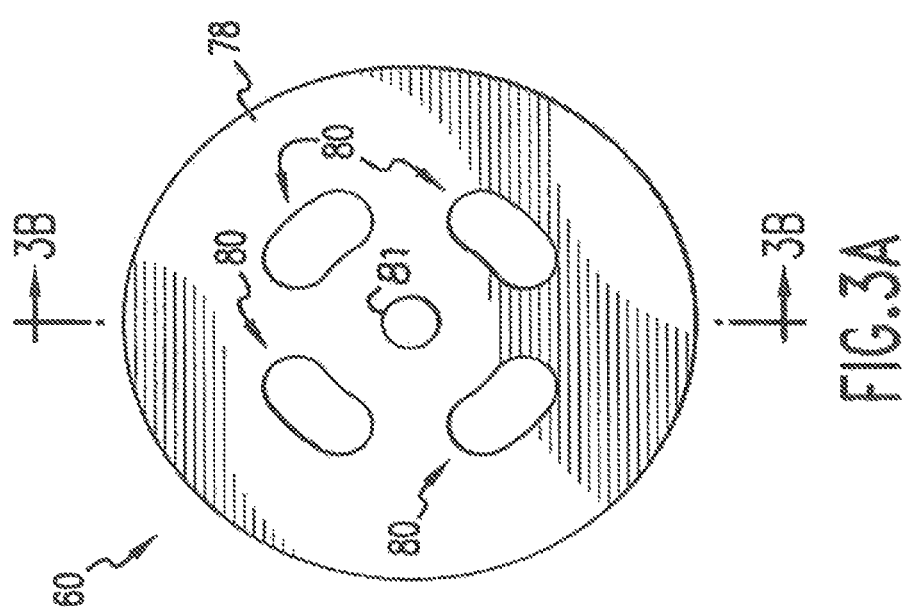

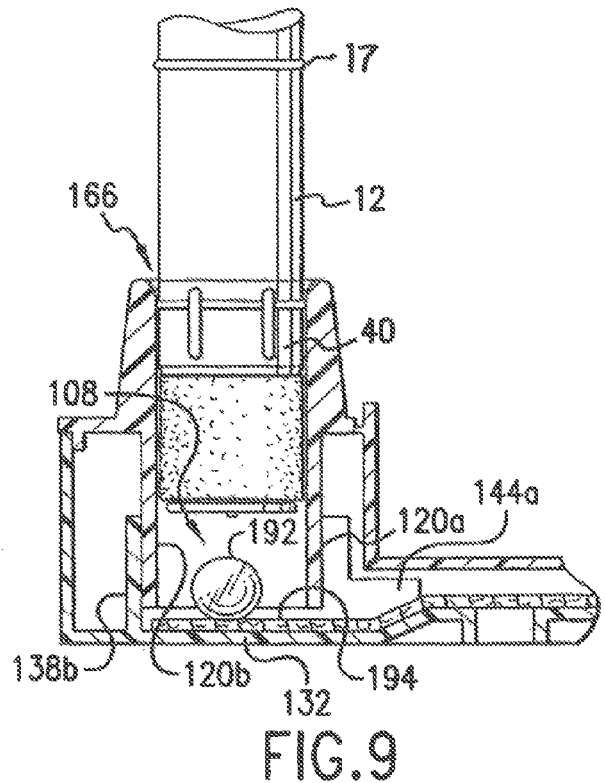
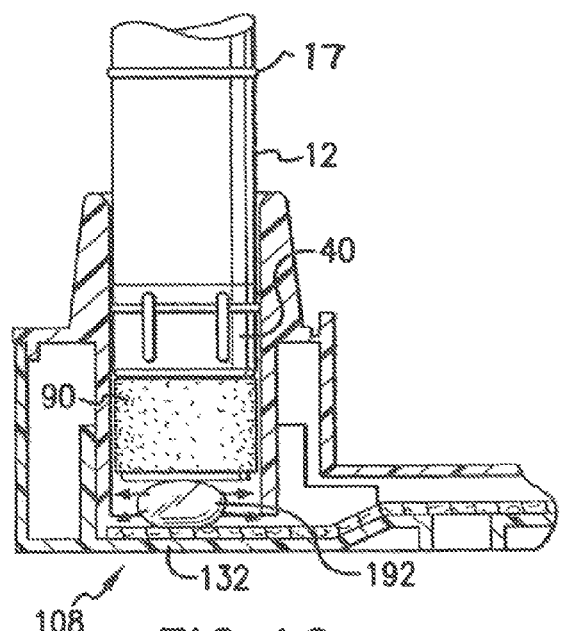
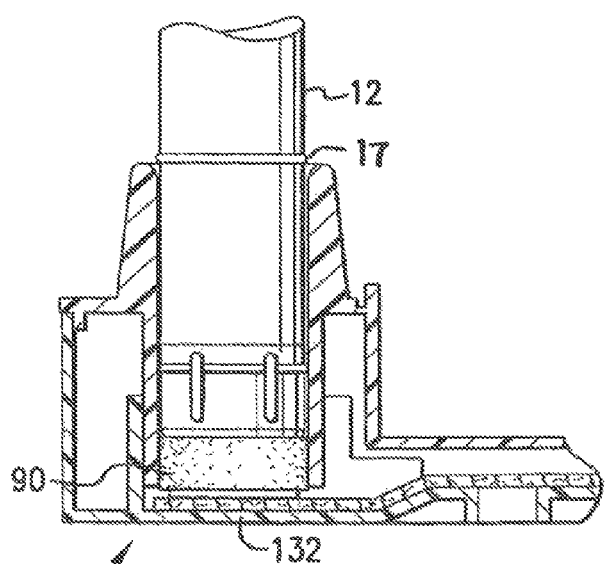

SAMPLE COLLECTOR AND TEST DEVICE

The invention relates to a sample collector, a test device and a combination thereof. The invention may be practiced in applications including the collection and assay of fluid samples, one example of which relates to the collection of a fluid sample using the sample collector and the delivery of the fluid sample to the test device for detecting the presence of analytes in the collected fluid sample.

BACKGROUND OF INVENTION

A number of devices for collecting and testing bodily fluids (e.g., blood, urine and saliva) for the presence of analytes exist in the art. En the context of providing a relatively quick and inexpensive sample collecting device and associated testing system, there exists several approaches for collecting a sample fluid, expressing the sample fluid in a test device and performing an assay of the sample. Examples of these types of testing systems include U.S. Pat. Nos. 5,965,453; 6,027,943; 4,895,808; 4,943,522; 6,267,722 and 5,393,496.

Diagnostic systems for performing an assay of an expressed sample typically include a sample collector, a container for holding the sample collector and a testing apparatus. One type of sample collector typically includes an absorbent pad for absorbing the target fluid and a holder for holding the sample as the sample is being collected. The sample is then transferred to a sample container or test device by using one of a variety of known approaches including a mechanism for expressing the sample into a sample container, U.S. Pat. No. 5,268,148, dipping the sample collector into a test solution, U.S. Pat. No. 4,895,808, or using a second filter or absorbent pad to transfer the fluid from the collector pad to an intermediate container or test device. Sample collectors may also include a sponge or chemical reagent disposed on a filter strip which may indicate that an adequate sample is collected, U.S. Pat. No. 5,393,496.

One type of test device for detecting the presence of analytes in a fluid sample is a lateral flow test device, an example of which is described in U.S. Pat. No. 6,027,943. The device for performing a lateral flow test device typically includes the lateral flow test strip, a port or opening for delivery of the expressed sample to the test device and a viewing area for viewing the test strip (the test strip indicating whether the targeted analyte is present in the fluid sample). The test device may, or may not also include a buffer solution for mixing with the sample and a second viewing area for confirming that there was an adequate permeation of sample through the test strip, U.S. Pat. No. 6,187,598. The presence or absence of the target analyte may then be determined by, for example, visual inspection under ambient light or by exposing the test strip to different forms of electromagnetic radiation using an instrument.

Lateral flow tests, also known as strip tests and immunochromatographic assays are often used in applications for home testing, rapid point of care testing, and field testing for different environmental and agricultural analytes. This technology offers a range of benefits including being user-friendly, relatively inexpensive and offering quick results. A lateral flow test strip is composed of four main elements: the sample application pad, the conjugate release pad, the lateral flow membrane and the support pad. These components are then enclosed within a test device housing which may contain a window or other means to read the assay results.

Solid phase lateral flow devices incorporate a solid support strip which binds a member of a ligand-receptor pair. Porous materials such as nylon, nitrocellulose, cellulose acetate, glass fibers, and other porous polymers are often employed as solid support strips. The sample that may contain the targeted analyte flows along the solid support across the assay. Several procedures may be utilized including the analyte or its derivative, becoming bound to the reactant and the presence of the analyte or its derivative being detected, or the analyte or its derivative may react to form a product that is then detected. Examples of detectable labels are various chromogens, such as fluorescence, dyes, absorbents which may or may not require an instrument for detecting the label.

SUMMARY OF INVENTION

The invention relates to a sample collector, test device for performing a lateral flow test and a diagnostic device for collecting and assay of an expressed sample using a lateral flow test. The diagnostic and/or test device of the invention may be used to detect the presence of multiple analytes in a single fluid sample. The multiple labeled reagents may test for drugs of abuse such as amphetamine, methamphetamine, benzoylecgonine, opiates, phencyclidine, or tetrahydrocannabinol. The diagnostic and/or test device of the invention may also be used to diagnose diseases such as giardia, mycoplasma, campylobacter, enteroviruses or influenza viruses, or allergies.

In one aspect of the invention, there is provided a diagnostic tool that collects a sample from a sample source, e.g., an oral cavity, expresses the sample into a lateral flow test device and provides immediate results. Applications for this diagnostic tool include quick and efficient employee screening procedures, periodic detection of drug use for paroles, inmates, and detainees. In the context of these and other possible uses (e.g., field testing by police officers of drug use), there are advantages to the diagnostic tool of the invention that include a easy-to-use and cost-effective design that may provide, among other things, a tamper resistant testing platform and an ability to effectively seal the collected sample within the test device so as to minimize the instances where an administer of the test may come into contact with the collected sample.

The invention includes a sample collector and test device. The sample collector and test device may be used together, or the sample collector and/or test device may be used separately with existing sample collectors, sample containers and test devices, respectively.

In one embodiment of the invention, a sample collector indicates when a sufficient volume of sample has been collected for assay. In this aspect of the invention, the size of the sample collector is compared with a reference size associated with the sample collector. If the size of the sample collector is approximately equal to the reference size, the user is informed that a sufficient volume of sample has been collected for assay of the sample.

In another embodiment of the invention, a sample collector provides a sample retention feature for retaining a second portion of sample for confirmatory testing after a first portion of sample has been expressed for assay.

In still another embodiment of the invention, an apparatus for assay includes a sample collector for containing a sample, a test cassette including a portal for receiving the sample and a test device for assay of analytes in the sample, and a means for preventing removal of the sample collector through the portal of the test device.

In still another aspect of the invention, an apparatus for assay of analytes in a sample includes a sample collector for collecting the sample, a collector holder for holding the sample collector, an elongate handle releasably securable to the collector holder, and a test cassette including a well adapted for receiving the collector holder and sample collector and engaging the collector holder so as to prevent removal of the sample collector from the well, and a test device disposed in operative proximity to the well for expression of the sample from the sample collector to the test device.

In still another aspect of the invention, a method for delivery of a sample to a tester for assay of the sample includes transferring the sample contained on a sample collector to the tester including the step of locking a collector holder in a well by engaging the collector holder and well, wherein the sample is discharged from the sample collector and placed in fluid communication with a tester.

In still another aspect of the invention, a method for collecting and assay of a sample collected from a sample source includes collecting the sample from the sample source by exposing both a sample collector and collector holder to the sample source, locking the collector holder and sample collector to a sample receiving area of a test device, and reading the results displayed on an assay strip.

Additional features and advantages of the invention will be set forth or be apparent from the description that follows. The features and advantages of the invention will be realized and attained by the structures and methods particularly pointed out in the written description and claims hereof as well as the appended drawings.

It is to be understood that both the foregoing general description and the following detailed description are exemplary and explanatory and are intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate preferred embodiments of the invention and together with the description serve to explain the principles of the invention. In the drawings:

FIG. 2A is a partial cut away view of the handle in FIG. 2 showing a portion of the locking feature for releasably securing the handle to the collector end.

FIG. 3A is an end view of the plunger of the collector end showing a disc with perforations for allowing sample to exit from a sponge when sample is expressed from the sample collector to a sample container and/or test device.

FIG. 3B is a cross-sectional view of the plunger taken along line 3B-3B in FIG. 3A.

FIG. 9 is a cross-section of a portion of the cassette with the collector in a first position in the opening of the cassette.

FIG. 10 is a cross-section of a portion of the cassette with the collector in a second position, inserted further into the cassette than in the first position, and shows the sponge compressing and an ampoule breaking.

FIG. 11 is a cross-section of a portion of the cassette with the collector in a third position, inserted further into the cassette than the second position, and shows the sponge compressed to a retained sample size configuration.

DETAILED DESCRIPTION OF THE PREFERRED EMBODIMENTS

Reference will now be made in detail to a preferred embodiment of the invention, examples of which are illustrated in the accompanying drawings. The invention includes collector 10 and cassette 100, as shown in its preferred embodiment in FIGS. 1-11. Collector 10 is of the type that is used to collect a liquid sample (hereinafter 'sample') such as oral fluid, blood, urine, or other liquid samples which may or may not be otherwise treated prior to being absorbed by collector 10. Collector 10 can be used alone or in combination with a cassette 100. Likewise, cassette 100 can be used with other sample collection and transfer devices. When used in combination, collector 10 is inserted into cassette 100 and the sample is transferred from the collector 10 to the cassette 100. Cassette 100 preferably includes a lateral flow test device that has the ability to detect target analytes in the fluid sample. The results from the lateral flow test may be identified either by the naked eye or by using an instrument. In the preferred embodiment, results are detected by using an instrument.

Figure 1:
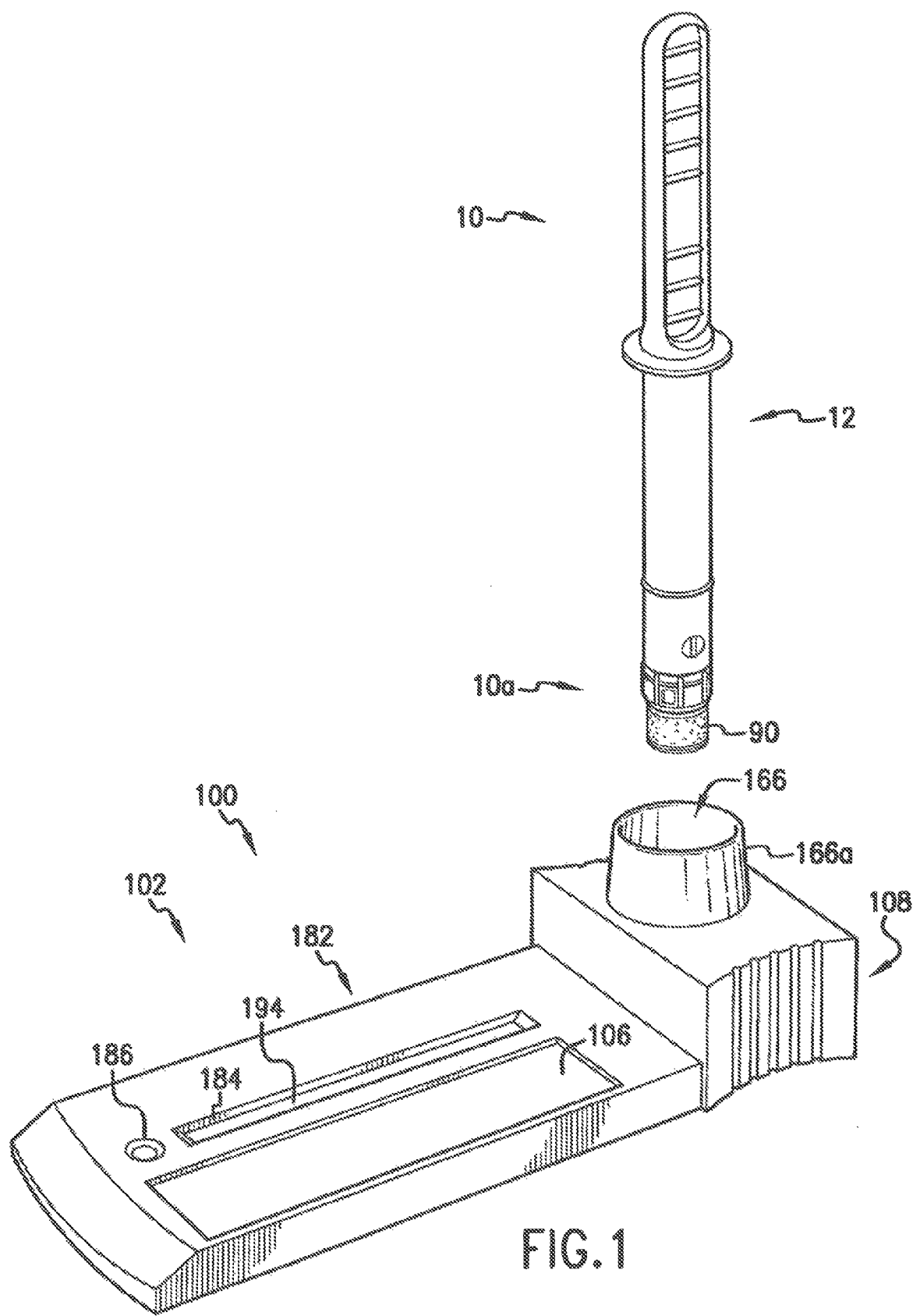
FIG. 1 is a perspective view of a preferred embodiment of a collector and cassette in accordance with the invention. The collector and cassette may be used together as a diagnostic device, or used separately with existing sample collectors or test devices, respectively.
Figure 2:
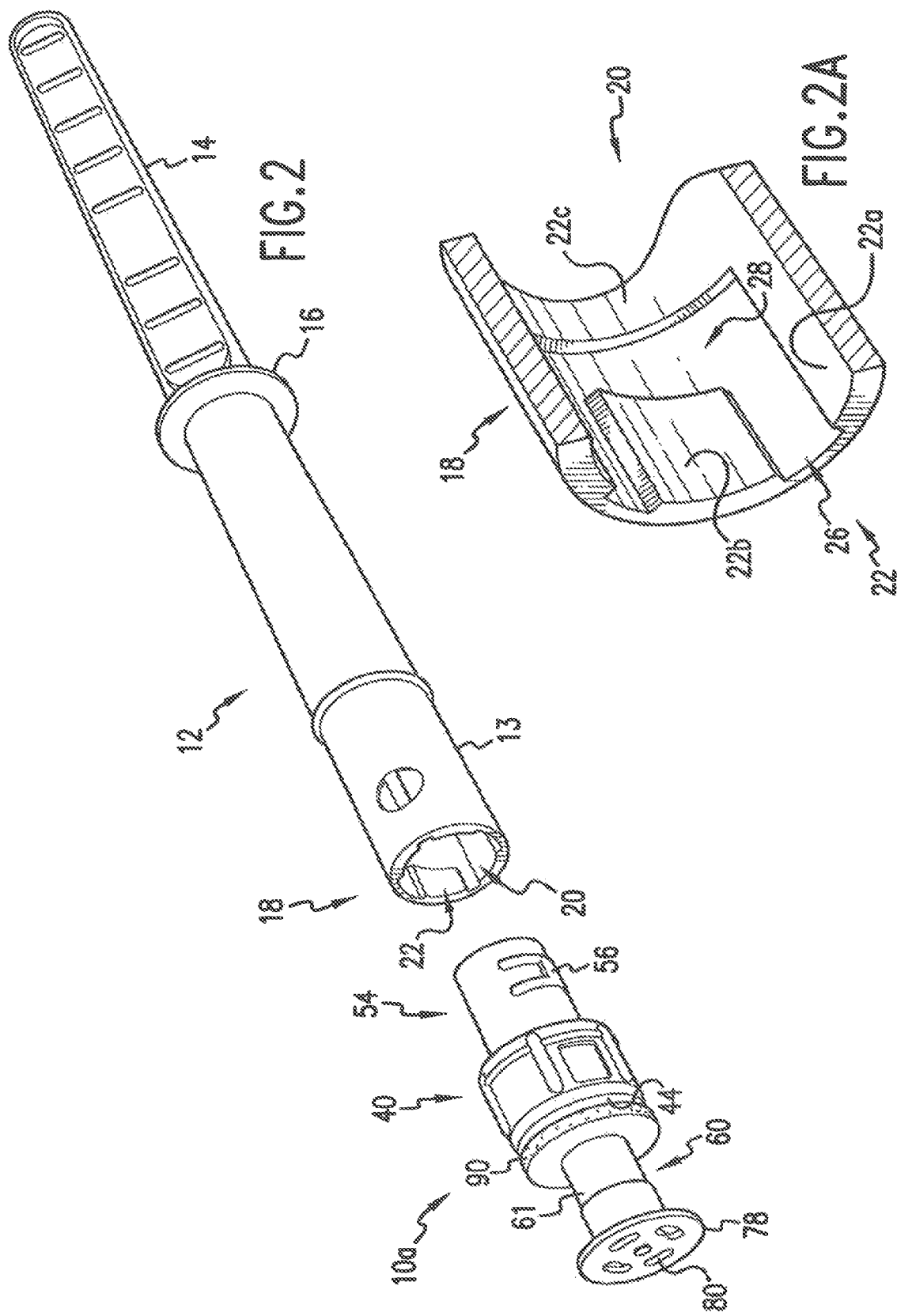
FIG. 2 is an exploded view of the collector of FIG. 1 showing the handle unlocked from the collector end.

Referring to FIG. 1, collector 10 generally includes a handle 12 detachably connected to a collector end 10a. A sponge 90 is disposed on collector end 10a to absorb the fluid sample, and, as shown in FIG. 1, is filled with sample. Collector end 10a of collector 10 is adapted for being received in an opening 166 of an upwardly extending section 166a of cassette 100 for transfer of, preferably, a portion of the sample into cassette 100. Referring to FIG. 2, collector 10 is shown in an exploded view with handle 12 detached from collector end 10a. A plunger 60 includes a disc 78 and a plunger arm 61 which retains a sponge 90 for collection of sample. Plunger arm 61 is slidably received in an opening formed in a plug 40. Collector 10a is adapted for expressing sample from sponge 90 by retraction of plunger arm 61 into plug 40. Disc 78 includes perforations 80 which function as nozzles allowing sample expelled from sponge 90 to pass through disc 78 when plunger arm 61 is retracted into plug 40.

Handle 12 will now be described in detail. In use, handle 12 is held by hand, for example, and collector end 10a is disposed in a sample source. For example, collector end 10a may be disposed in an oral cavity to absorb saliva, or collector end 10a may be exposed to sample in a container, e.g., when collecting a sample of blood or urine. Handle 12 is preferably configured to facilitate collection of a sample from an oral cavity. Handle 12 includes a barrel portion 13 having a grip 14 extending from one end and an open end 18 adapted to receive collector end 10a. Between barrel portion 13 and grip 14 is an annular flange 16 to block fluid which may accumulate on barrel 13 and flow towards grip 14 during sample collection, e.g., saliva collection from an oral cavity. Grip 14 may include ribs 14a or other structure so that handle 12 may be securely gripped when collector 10 is inserted and reinserted into the oral cavity, for example.

Handle 12 may be removably attached with collector end 10a using a luer-type lock. Inside open end 18 of handle 12 is one example of a luer-type lock structure for engaging corresponding structure on collector end 10a. A first half of wall section 22 of open end 18 is shown in FIG. 2A. The other half of this wall section (not shown in FIG. 2A) is a mirror image of wall section 22. Wall section 22 includes a first raised portion 22a, second raised portion 22b and third raised portion 22c, together defining a substantially L-shaped groove including a vertically extending first groove portion 26 and a laterally extending second groove portion 28. Groove portions 26 and 28 are sized to receive and releasably lock with a protrusion 56 formed at a handle end 54 of collector end 10a.

More specifically, handle end 54 of collector end 10a is formed on an outer wall surface of plug 40. As shown, protrusion 56 is generally U-shaped and may have an increased taper from the open end of the U-shape toward the closed end. A second protrusion (not shown) is formed on an opposing side of handle end 54 for mating with a corresponding L-shaped groove formed on the wall section opposing wall section 22. The L-shaped groove formed in wall section 22 may also include a detent for added locking force between collector end 10a and handle end 18. Handle end 54 of collector end 10a is mated with open end 18 by positioning handle end 54 such that protrusion 56 is aligned with first groove 26. Handle end 54 is then pushed into opening 20 of open end 18 so that protrusion 56 is pushed into groove 26 until protrusion 56 contacts third raised portion 22c. Handle 12 and/or collector end 10a are then rotated causing protrusion 56 to be pushed into second groove 28. Handle 12 is then rotated until protrusion 56 forms a tight fit within groove 28, which is preferably tapered. Collector end 10a is now sufficiently retained on open end 18 so that collector end 10a may be delivered to a sample source and then to a sample container and/or test device for sample expression without inadvertently detaching from handle 12.

Other structural arrangements may be used and other types of locking mechanisms may be used in accordance with the invention so that collector end 10a is reliably secured to handle 12 for use, yet is removable for testing purposes. In other embodiments, plug 40 may have grooves for receiving protrusions formed on open end 18 and/or open end 18 may be received in an opening formed in handle end 54. In still another embodiments, one or both of open end 18 and handle end 54 may include a flexible tab or button lock, disengaged by either finger pressure applied locally or by engaging collector 10 with a contact surface formed on a sample container and/or test device, the contact surface being adapted for disengaging the lock or tab. Plug 40 may also be secured to handle 12 by providing complimentary threads in plug 40 and handle 12 so that plug 40 may be secured to handle 12 by rotating handle 12 about plug, thereby engaging the threads formed on the inner surface of handle 12 with corresponding threads formed on plug 40.

In the preferred embodiment, plunger 60, plug 40 and sponge 90 of collector end 10a are constructed to provide an indication of sample adequacy for collector 10, a mechanism for expressing fluid from sponge 90 when delivering the expressed sample to a sample container and/or test device, such as cassette 100, and a mechanism for delivery of a first portion of sample for assay while retaining a second portion of sample for subsequent assay. Handle 12 is adapted for delivery of plug 40, plunger 60 and sponge 90 to a sample source, e.g., an oral cavity, and is preferably releasably securable to plug 40, as discussed above, so that plug 40, plunger 60 and sponge 90 containing the collected sample may be delivered and kept with a sample container and/or test device. Handle 12 may then be removed.

Figure 3:
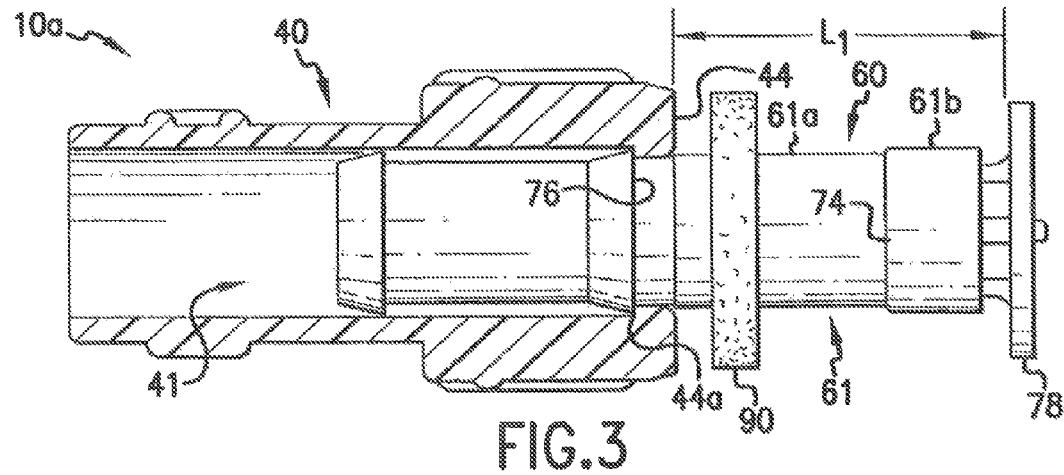
FIG. 3 shows the collector end with the plug in cross-section to show the plunger disposed therein.

Referring to FIG. 3, collector end 10a is generally of a plunger-type construction including plug 40 adapted for slidably receiving plunger arm 61 of plunger 60 into a channel 41 of plug 40. As discussed above, plug 40 includes a handle end 54 for insertion into open end 18 of handle 12. An end wall 44 of plug 40 defines an opening for slidably receiving plunger 60 within channel 41. In particular, plunger 60 includes a plunger arm 61 with a first diameter portion 61a adapted to slidably fit into the opening defined by end wall 44 of plug 40 when sample is expressed from sponge 90, a second diameter portion 61b, having a larger cross-section diameter than first diameter portion 61a, and a recess 61c (having a slightly reduced cross-section diameter, less than the diameters associated with portions 61a and 61b) which is engaged with end wall 44 when sample is being collected on sponge 90.

First and second flange portions 76 and 77 are formed on a portion of plunger arm 61 which is intended to permanently reside within channel 41 of plug 40. Flange portions 76 and 77 are preferably formed to minimize the risk of plunger 60 being dislodged from plug 40 during sample collection. Flange 77 is formed in addition to flange 76 as an added safety precaution to prevent removal of plunger 60 from plug 40 (e.g., as in the case where collector 10 is used to collect saliva from an oral cavity) and may be thought of as a redundant stop in the event that flange 76 breaks through end wall 44 during sample collection. Flange portion 77 additionally helps to guide plunger 60 as plunger 61 slides within channel 41 by abutment of flange 77 with the inner walls of channel 41 as plunger aria 61 slides within channel 41. A proper sliding of plunger arm 61 within channel 41 is further encouraged by sizing first diameter portion 61a such that a loose friction fit is promoted between portion 61a and end wall 44 as plunger arm 61 slides within channel 41.

Figure 5:
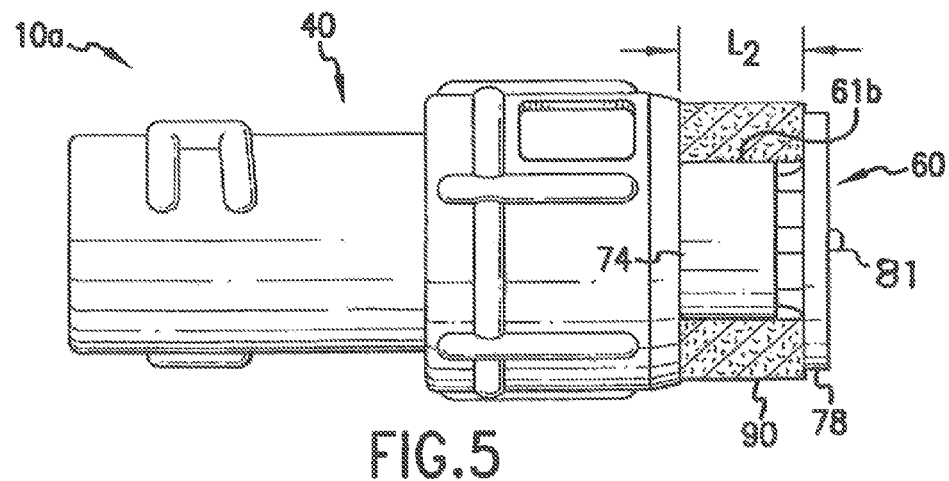
FIG. 5 is the collector end in a retracted configuration after expression of a portion of the sample, the sponge having a retained portion of sample and the sponge being shown in a cut-away view for purposes of illustration.

The amount of the movement of plunger 60 along the longitudinal axis of collector end 10a is controlled by flange 76 and expanded diameter portion 61b. When flange wall 76a is engaged with inner surface 44a and recess 61c is disposed within the opening formed by wall end 44, wall 78a of disc 78 is at a length $L_1$ from end wall 44, as illustrated in FIG. 3, which corresponds to the position of plunger 60 relative to plug 40 during sample collection. When wall 74 of second diameter portion 61b is engaged with end part 44, disc wall 78a is positioned at a distance $L_2$ from end wall 44, as shown in FIG. 5.

Disc 78 is disposed on the end of the second diameter portion 61b and is spaced from the second diameter portion 61b by circumferentially spaced extensions 79 which, together with holes 80 formed in disc 78, define fluid passageways for collector end 10a for sample expressed from sponge 90. A bump 81, formed at the center of disc 78, engages with a contact surface (e.g., the bottom surface of a sample container) when sample is expressed from sponge 90, as discussed below. Bump 81 is preferably formed so that when disc 78 mates with the contact surface, disc 78 is spaced above the contact surface so that expressed sample may exit from holes 80. Referring to FIGS. 3A and 3B, which shows an end view of collector end 10a and cross-sectional view taken along lines 3B-3B in FIG. 3A, four angularly-spaced holes 80 are formed in disc 78. The fluid passageways for expressed sample formed by openings 80 and spaced extensions 79 allow a portion of expressed sample to exit directly from the center of disc 78 to the portion of the sample container and/or test device opposing disc 78. It is desirable to provide fluid passageways for allowing fluid to exit directly from disc 78 when, for example, collector 10*a* is used to delivery a sample to a lateral flow test device since sample may be delivered directly to an assay strip by engaging bump 81 directly to an absorbent pad, as in the preferred embodiment (discussed below). Sample may also pass over an outside edge of disc 78.

Figure 4:
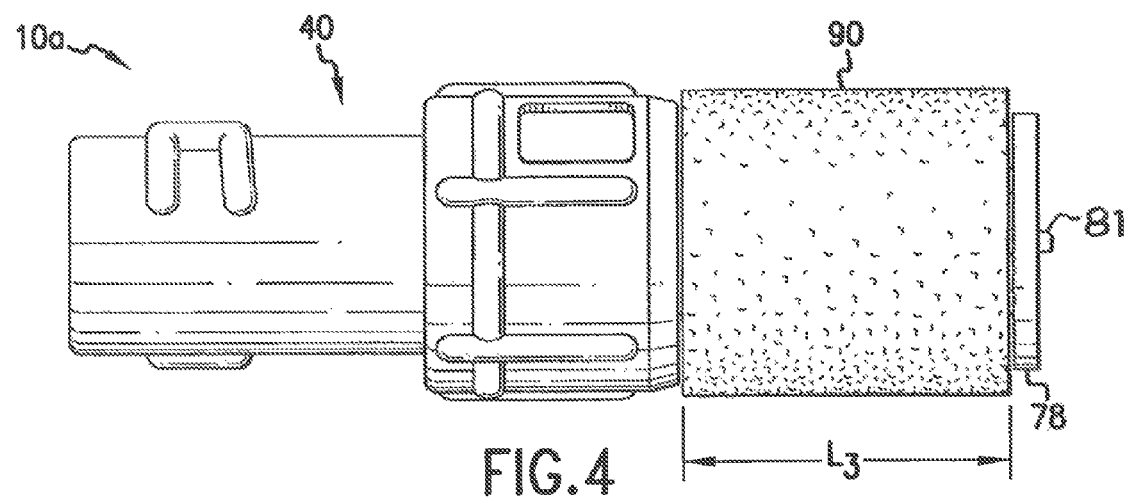
FIG. 4 is the collector end in the expanded configuration after the sponge has absorbed an adequate amount of sample for assay.

In the preferred embodiment, a sponge 90 is slidingly retained on the portion of cylindrically shaped arm 61 of plunger 60 that extends between disc 78 and end wall 44. Sponge 90, prior to absorbing fluid sample, is of a generally cylindrical, thin disc shape and is snugly fit to first diameter portion 61*a*, as shown in FIG. 3. Sponge 90 is an expandable type sponge so that as it absorbs liquid, sponge 90 expands to an enlarged size, both radially and longitudinally. Sponge 90 may be made from any suitable fluid absorbing material. Sponge 90 may be treated with agents to promote the extraction of fluid from a sample source as in, for example, where collector 10 is used to collect a saliva sample from an oral cavity. In this case, sponge 90 may be treated with an agent that promotes saliva production within the oral cavity. In the preferred embodiment, sponge 90 expands longitudinally as it absorbs sample. When sponge 90 has collected a sufficient volume of sample for assay, sponge 90 will have grown from a dry size, as shown in FIG. 3, to an expanded size such that its length $L_3$ extends approximately between end wall 44 and disc 78, as shown in FIG. 4. As can be seen, sponge 90 also exhibits a growth in the radial direction such that sponge 90 will slightly extend over the edges of disc 78. When sponge 90 has accumulated a sufficient volume of sample for assay, sponge 90 may extend over second diameter portion 61*b*.

As mentioned above, collector 10 is preferably constructed to inform a user of sample adequacy when a sufficient sample volume is collected for assay. Preferably, sample adequacy is determined by comparing the size of sponge 90 when sample is contained therein to a predetermined size defined by plunger 60 and plug 40. Referring to FIG. 3, as shown the distance between disc 78 and end wall 44 has a length of $L_1$. Sponge 90 expands from its dry thin disc-shaped configured to this expanded configuration as it absorbs sample. FIG. 4 shows sponge 90 fully expanded to a length $L_3$. As shown, $L_3$ is approximately equal to $L_1$. When the sponge size $L_3$ defines a length approximately equal to $L_1$, an adequate sample is collected. The user can see that sponge 90 approximately fills the distance between disc 78 and end wall 44. In another embodiment, sample adequacy may be determined by visual inspection of one or more indicia (e.g., first and second colors) formed on the outer surface of plunger arm 61. In such an embodiment, sample adequacy may be determined when one or both of the indicia are hidden from view when an adequate sample is contained in sponge 90. In another embodiment, a longitudinally extending member, not necessarily formed by, or constituting part of plunger 60, but which is disposed (or disposable) within proximity of sponge 90 and extends (or is extendable) along a direction generally parallel to a longitudinal axis (e.g., the longitudinal axis of plunger 60 in FIG. 3) may be used to determine whether a sufficient volume of sample is collected for assay. One example of a longitudinally extending member is a transparent sleeve having formed thereon first and second spaced indicia which indicate a sponge size corresponding to a sample volume sufficient for assay. Sample adequacy may then be determined by disposing sleeve over sponge and comparing sponge 90 size to the reference size defined by the space between the first and second indicia. If sponge 90 fully occupies the space between the first and second indicia, then an adequate volume of sample is collected for assay. Thus, the invention contemplates that any suitably sized member associated with collector 10 may be used to determine whether the size of sponge 90 is such that an adequate volume of sample has been collected for assay by comparing a reference size to the size of sponge 90. It is preferred, although not necessary, to use the distance between disc 78 and end part 44 as the reference size. Further, it is preferred, although not necessary, to compare a reference length to the longitudinal expansion of sponge 90.

As discussed above, collector 10 is preferably provided with a retractable plunger 60 for expression of sample from collector 10 into a sample collector and/or test device, such as cassette 100. When an adequate sample has been collected for assay in the preferred embodiment, sample may be expressed from sponge 90 by engaging bump 81 of disc 78 with an engagement surface provided on the sample container and/or test device and firmly pressing down against this engagement surface. When sufficient pressure is applied to the sample container and/or test device engagement surface (which may correspond to the bottom surface of a sample container containing a sample treatment solution), first portion 61*a* of plunger 61 is pushed into channel 41 until disc 78 is disposed at distance $L_2$ from end wall 44 as shown in FIG. 5. During this displacement of plunger 60, sample is expressed from sponge by the compressive forces exerted on sponge 90 by disc 78 and end wall 44. The frictional fit formed between first diameter portion 61*a* and end wall 44 will discourage sample from entering into channel 41 as sponge 90 is squeezed between end wall 44 and disc wall 78*a*. Although a majority of the expressed sample will flow over the outer edges of disc 78 when sponge 90 is compressed, the fluid passageways formed by extensions 79 and holes 80 formed in disc 75 will also allow a portion of sample to exit directly from disc 78 to the surface portion directly adjacent to bump 81.

In the preferred embodiment of the collector 10 being used with cassette 100 to delivery and assay sample (as discussed in greater detail below), when sample is expressed from collector 12 to cassette 100, plunger arm 61 is pushed into channel 41 by engagement of bump 81 with a sample receiving pad portion of an assay strip disposed in cassette 100. As discussed above, by providing fluid passageways formed by extensions 79 and holes 80 and by using a bump 81 to engage the sample receiving pad (which creates a space between disc 78 and the sample receiving pad for fluid flow), a portion of sample is advantageously delivered directly to the sample receiving pad of the assay strip. Other known approaches for expression of sample from collector 10 may be used without departing from the scope of the invention. For example, in one embodiment collector 10 may not use a retractable plunger for expression of sample from a sponge. In this embodiment, the sample contained in collector 10 could be expressed by engaging collector 10 with device that creates a pressure differential (e.g., a pump) for delivering sample from collector 10 to a secondary container and/or test device. Further, in the embodiments which use a sponge to collect sample, e.g., the preferred embodiment, collector 10 may be inserted into a conical or other suitably-shaped contact surface such that the sample is expressed by pressing the sponge into the contact surface.

As mentioned earlier, collector 10 provides a mechanism for expression of a first portion of sample for assay while retaining a second portion of sample in sponge 90 for a second assay, such as for confirmatory testing of results from the first assay of sample. Such a sample retaining feature is preferably implemented by forming second diameter portion 61*b* of plunger arm 61 defining a wall 74 which engages with end part 44 when sample is expressed from sponge 90 as described above. Thus, raised portion 61*b* will prevent sponge 90 from being fully compressed between disc 78 and end wall 44 when collector is pressed into a contact surface, e.g., a bottom wall of a sample container. After expression of a first portion of sample, FIG. 5, the retained sample may then be retrieved for later confirmatory testing by collecting collector end 10a from the sample container and/or test device. The amount of retained sample may be increased or decreased by increasing or decreasing the length of second portion 61b so as to increase or decrease, respectively, the corresponding distance $L_2$ between end part 44 and disc wall 78a after expression of the first portion of sample.

Figure 6:
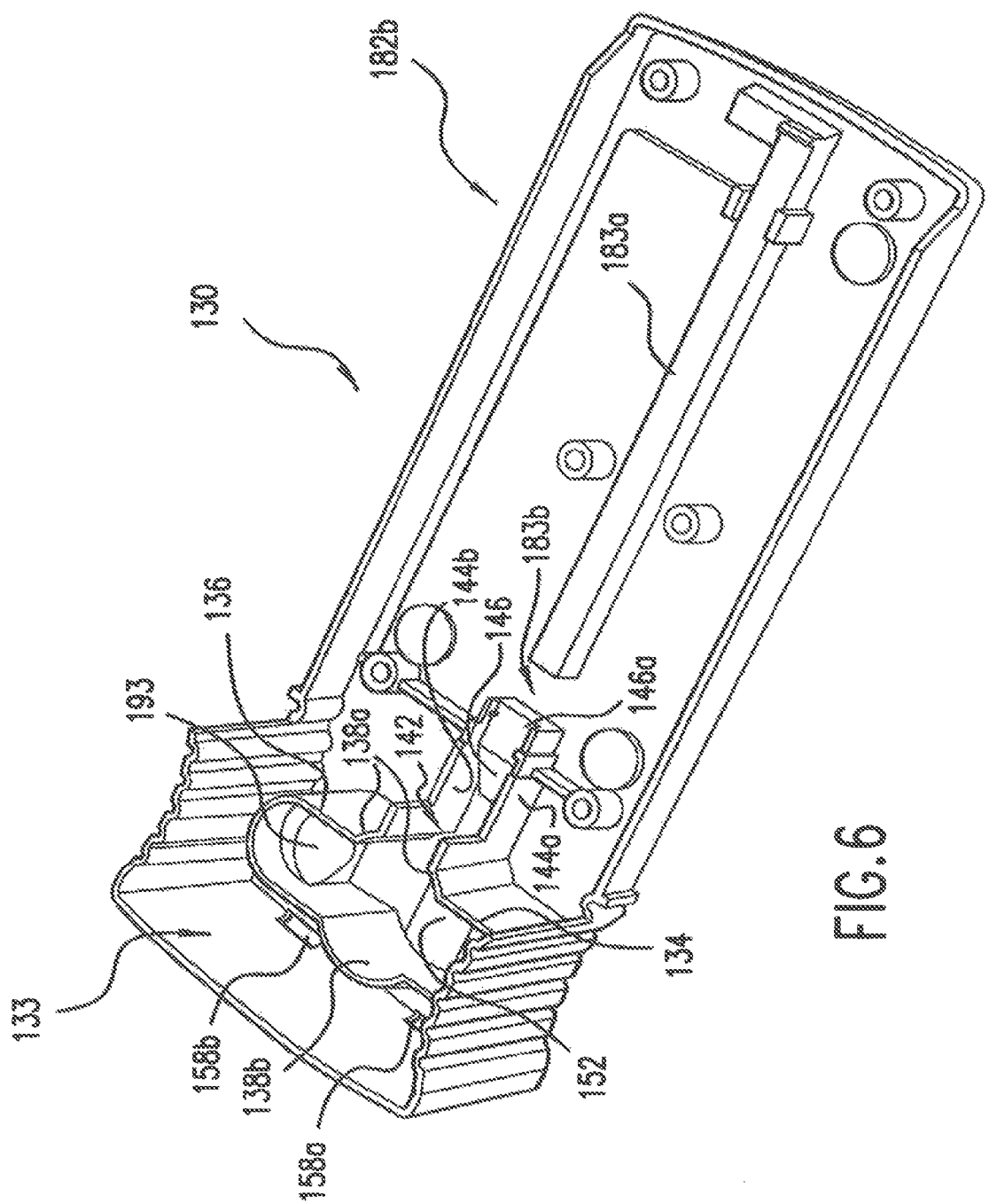
FIG. 6 is a perspective view of the inside of a lower housing of the cassette of FIG. 1.

A detailed description of cassette 100 follows. Referring to FIG. 1, a preferred embodiment of cassette 100 includes a housing 102 formed by mating an upper housing 110 (FIG. 7) and a lower housing 130 (FIG. 6). Housing 102 provides a generally circular entrance opening 166 for receipt of a sample collector, preferably collector 10. Entrance opening 166 provides access to a well area formed by a well portion 108 (as illustrated in FIGS. 9-11) of housing 102 for retaining the collected sample expressed from the sample collector. Well portion 108 is contained within a box-like well portion housing 108a, as shown in FIG. 1.

A lateral assay strip 194 (viewable through windows 184 and 186 formed in housing 102) is disposed in cassette 100 for detecting target analytes in an expressed sample. In the preferred embodiment, assay strip 194 is a sandwich-type or competitive-type assay strip including four primary components supported on a polystyrene support strip: a sample receiving pad and a conjugate release pad, a porous nitrocellulose solid support for binding the various ligand-receptor pairs associated with the targeted analytes, and an absorbent pad that provides a reservoir for fluid that migrates through the nitrocellulose solid support through capillary action. Other types of assay strips may be used. The various aspects of cassette 100 or other embodiments of a test device that are within the scope of the invention do not depend on the specific type of lateral assay test performed using, or assay strip used with cassette 100. The following discussion will therefore describe assay strip 194 only in terms of its sample receiving portion (a porous pad which is placed in direct fluid communication with the expressed sample), test portion (the porous solid support containing ligand-receptor pairs), and the absorbent pad (the pad that provides a fluid reservoir). An example of methods, compositions and apparatus for detecting analytes, in particular sensitive detection of multiple analytes, that can be used in accordance with the invention is disclosed in U.S. Pat. Nos. 5,698,397; 5,736,410; and 5,891,656 to Zarling et al., the disclosures of which are incorporated herein by reference in their entirety.

Referring again to FIGS. 1 and 7, the test portion and absorbent pad of assay strip 194 are contained an assay portion 182 of housing 102 which extends from well portion housing 108a. Test portion of assay strip 194 is viewable through a laterally extending window 184 formed on upper housing 110 for visual inspection of test results (either by the naked eye or using an instrument). A second circular window 186 is also formed on assay part 182 and is disposed above the absorbent pad of assay strip 194 so that a user can confirm that a successful test was run. Preferably, a strip line of water soluble dye is disposed between the junction of the absorbent pad and test portion of assay strip 194. As the sample migrates through the test portion and is collected in the absorbent pad, the dye will dissolve into the sample, thereby providing a visual indication of when the test is complete. A completed test may then be indicated by a coloration formed in the absorbent pad that is viewable through window 186 by the naked eye. Other types of indicia known in the art may also be used, depending on needs.

Well portion 108, shown in FIGS. 9-11, is contained within well portion housing 108a and preferably defines a well area describing a semi-enclosed region for mixing a sample treatment solution with the expressed sample and also minimizes the amount of sample entering into assay portion 182, other than by capillary action. Sample receiving portion of assay strip 194 is contained within well portion 108 and partially extends into assay part 182, as described below.

In the preferred embodiment, cassette 100 is provided with a recessed area 106 formed on upper housing 110 (see FIG. 1) for receiving a label strip. The label strip may be used to identify the sample source, e.g., patient information, and date of test. A second recessed portion is also formed on the outer surface of lower housing 130 (i.e., the bottom face of housing 102) of the preferred embodiment for receiving a label strip containing test related information, preferably a bar code strip. This second recessed portion may be used to identify, e.g., the lot number of the cassette, calibration information relating to test results and the test type.

Figure 8:
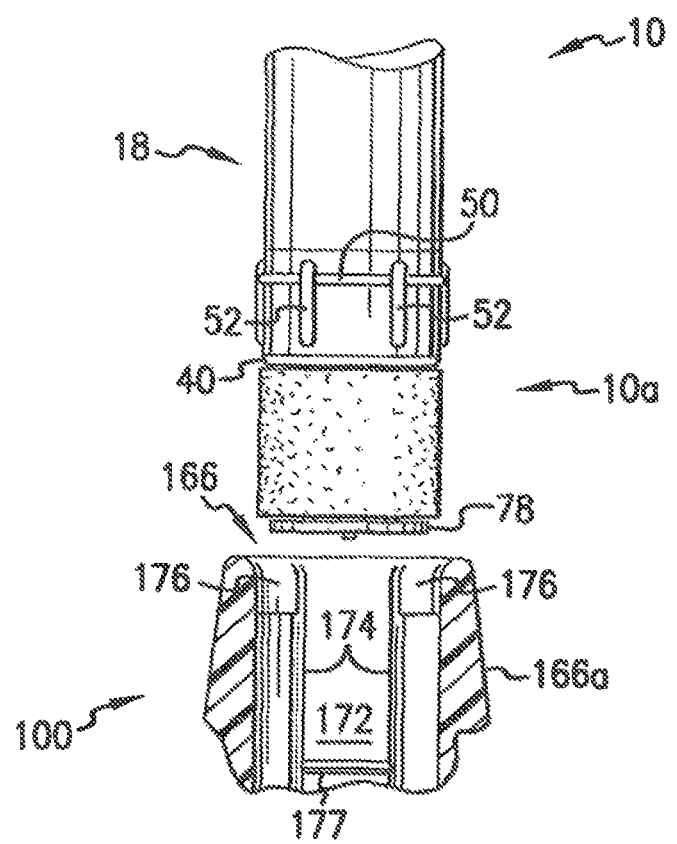
FIG. 8 is a portion of the collector positioned above an opening of the cassette in the cross-section.

An upwardly extending section 166a, formed on the top surface of well portion housing 108a, provides an opening 166 for receiving the sample collector and/or delivery device, such as collector 10. The well portion 108 of housing 102 is accessible through upwardly extending section 166a. FIG. 8 shows a cross-section of upwardly extending portion 166a. Opening 166 is generally rounded so that a sample collector may be easily guided into upwardly extending section 166a. A channel is formed within upwardly extending section 166a below opening 166. Referring to FIG. 8, in the preferred embodiment, channel walls 172 include grooves 174, ledges 176 and a ridge 177 formed in channel walls 172 for receiving and engaging corresponding vertical ridges 52 and a circumferential ridge 50 formed on plug 40 of collector 10, as will be explained in greater detail below. Thus, the preferred embodiment of cassette 100 includes engagement surfaces for engaging collector end 10a. Channel walls 172 of cassette 100 may alternatively have other types of engagement surfaces for engagement with a sample collector, e.g., threaded grooves for engagement with corresponding threads disposed on a sample collector, or none at all. In arty case, a sample may be delivered to the well portion of cassette 100 by, for example, expressing a sample into opening 166 using a syringe or other suitable sample collecting and/or delivery devices such as a pipette.

Figure 7:
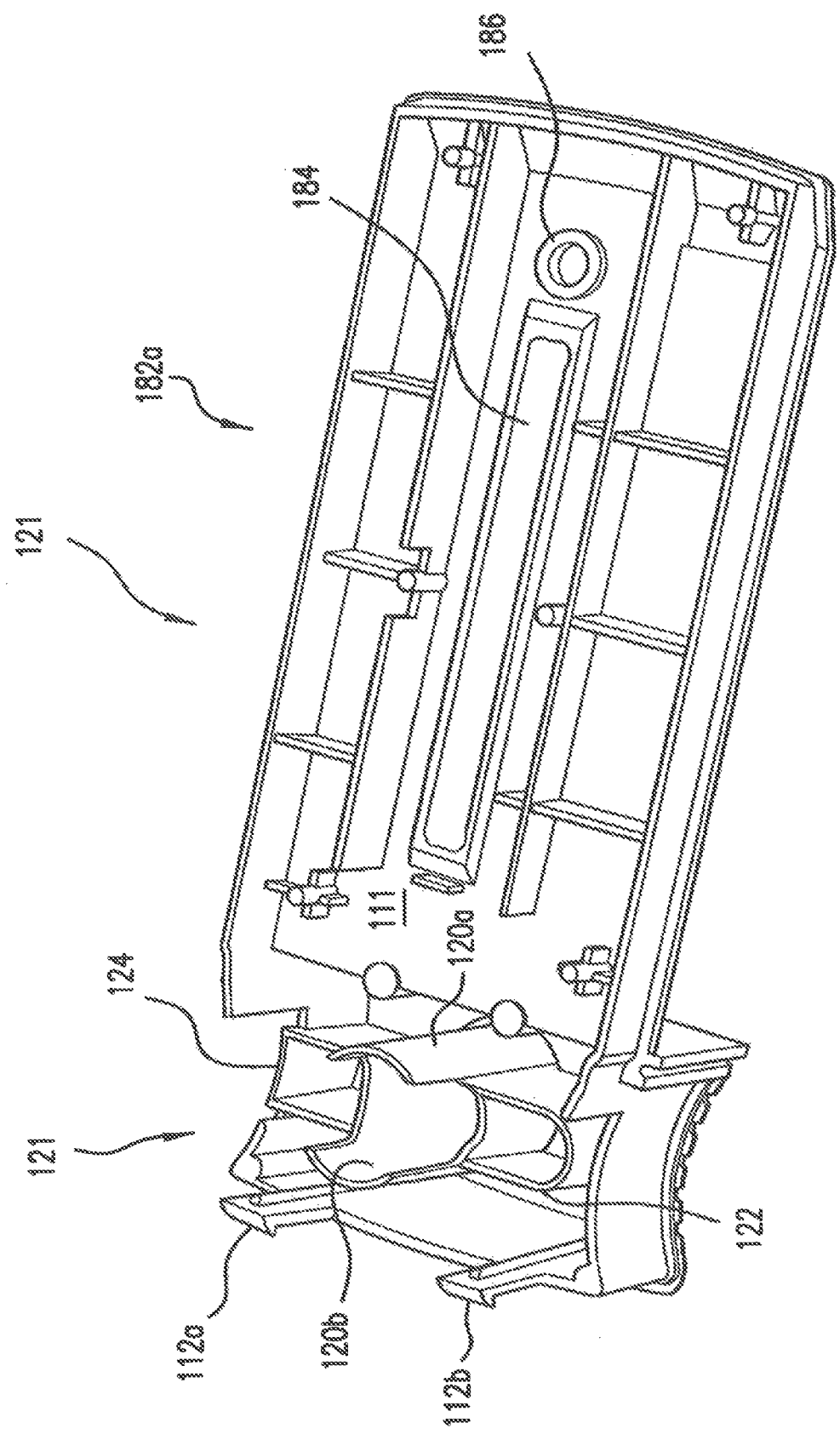
FIG. 7 is a perspective view of the inside of an upper housing of the cassette of FIG. 1.

Referring to FIGS. 6 and 7, housing 102 of cassette 100 is assembled by mating an upper housing 110 with a lower housing 130. Housings 110, 130 are preferably made from plastic and formed by injection molding. Referring to FIGS. 1, 7 and 8, upper housing 110 includes upwardly extending section 166a, walls 172 (which may include walls 120a, 120b as shown in FIG. 7) describing the generally cylindrical shaped channel extending from opening 166 into well portion 108, an upper well portion 121 defining the upper portion of the well portion 108, and an upper assay portion 182a of assay part 182 including viewing window 184 and circular window 186. Referring to FIG. 6, lower housing 130 includes a lower well portion 133 forming the lower portion of the well portion 108 including a fluid port 142 defined by opposed walls 144a, 144b and a ramp 146. Fluid port 142 defines a lower part of an exit passage for the sample receiving portion of assay strip 194 from the well portion 108 to assay portion 182. Lower assay part 182b of lower housing 130 (generally referring to the portion of housing 130 exterior of the well portion 133, walls 144a and 144b and ramp 146 defining the lower well part 182b) includes a platform 183a for supporting the assay strip and a canyon 183b defined by the space between platform 183a and a ramp ledge 146a.

Housing 110 includes flexible tabs 112a, 112b which engage with corresponding slots 158a, 185b on lower housing portion 130 which lock housing 130 and 110 together during assembly. Tabs 112a, 112b may be pushed through slots 158a, 158b to separate housing 130 from housing 110, such as when a portion of sample is to be retrieved from well area for confirmatory testing when collector 10 is used with cassette 100, as described below.

As mentioned above, housing 102 preferably forms well portion 108 defining a well area. Well area refers to the space enclosed by well portion 108 for receiving sample expressed from a sample collector. Well portion 108 is preferably formed in cassette 100 to minimize excessive sample and/or sample and treatment solution (depending on the assay to be performed) from entering into assay portion 182. Well portion 108 is formed by upper well portion 121 and lower well portion 133 when upper housing 110 and lower housing 130 are mated together. Specifically, a right upper well portion 124, describing a rectangular type enclosure, is received within a left lower well portion 134 part having a complimentary rectangular type enclosure, a left upper well portion 122, describing a U-shaped enclosure is received within a right lower well portion 136 having a complimentary U-shaped enclosure, and channel extensions 120a, 120b formed on upper housing 110 are received between complimentary curved walls 138a and 138b formed on lower housing 130. When housings 130, 110 are mated together, channel extensions 120a, 120b are disposed slightly above a lower well wall 132, as shown in FIG. 9.

Referring to FIGS. 6 and 9, well portion 108 is preferably shaped to receive a cylindrical ampoule containing a treatment solution for mixing with the expressed sample. Referring to FIG. 6, a right ampoule ledge 193a and opposed left ampoule ledge (not shown) are formed on lower well wall 132 to support ampoule 192 above lower well wall 132 and provide a space between ampoule 192 and lower well wall 132 for receiving the sample receiving portion of assay strip 194 directly beneath ampoule 192, as shown in FIG. 9. In a preferred use of cassette 100, ampoule 192 is crushed by disc 78 and bump 81 of collector end 10a as sample is expressed from sponge 90, thereby releasing the treatment solution and mixing the treatment solution with the expressed sample in the vicinity of the sample receiving portion of assay strip 194. The enclosure defined by well portion 108 retains fragments of ampoule 192 that remain after expression of the sample within well area and minimizes expulsion of treatment solution and/or sample into assay part 182, other than through capillary action through the test portion of assay strip 194.

Referring to FIGS. 6 and 9, a narrowed exit passage 147 provides a passageway for assay strip 194 from well portion 108 into assay portion 182. Exit aperture 147 is sized slightly larger than assay strip 194 and is raised above lower well wall 132 so as to minimize flooding of sample into assay 182. Referring to FIGS. 6, 7 and 9, exit passage 147 is defined by walls 144a, 144b, ramp 146 and inner surface 111 of upper housing assay part 182a. Canyon 183b, referring to the space between ramp ledge 146a and a left end of platform 183a in FIG. 6, is preferably formed to prevent sample and/or mixed sample and treatment solution from flowing along the bottom of the test strip and platform 183a by capillary action to the end of the test strip and wetting the end or sides of the nitrocellulose solid support before sample migrates through the strip as intended (e.g., if cassette 100 were accidentally tipped forwardly during assay), thereby potentially corrupting results displayed on assay strip 194.

As mentioned above, in the preferred embodiment of a diagnostic device, collector 10 is used to collect sample and cassette 100 receives the expressed sample and provides assay of the expressed sample. This preferred diagnostic device will now be described in detail with reference to the previously described features of collector 10 and cassette 100. Collector 10 and cassette 100 are understood as exemplary only of the various features of invention set forth in the appended claims and that the examples of invention provided by the prior description of collector 10 and cassette 100 are to be considered separate and distinct from the aspects of invention exemplified by the preferred diagnostic device now discussed in detail. Accordingly, both collector 10 or cassette 100 exemplify aspects of invention relating to a diagnostic device, in addition to a sample collector and a test device of the invention.

Referring to FIG. 8, channel walls 172 of upwardly extending section 166a, which define an entrance passage to the well area 10a, include a locking feature that allows plug 40, plunger 60 and sponge 90 to be lockingly retained within the channel. In the preferred embodiment, channel walls 172 include a set of three ledges 176, spaced approximately 120° apart and disposed near opening 166, six, equally spaced, vertically extending grooves 174 placed 60° apart, extending downwardly from opening 166, and a two lower ridges 177, spaced 180° apart and located below ledges 176. Ledges 176, grooves 174 and ridges 177 are preferably formed integrally with channel walls 172. Plug 40 includes six corresponding vertical ridges 52 for engagement with grooves 174 and a circumferential ridge 50 extending about the circumference of plug 40 for engagement with ledges 176 and ridge 177.

Collector end 10a is locked into channel by first aligning grooves 176 with ridges 52 and then pressing collector end 10a into opening 166 so as to displace circumferential ridge 50 below ledges 176. Once ridge 50 is clear of ledges 176, the lower surfaces of ledges 176 will inhibit removal of collector end 10a from opening 166. The channel is sized to form a friction fit between plug 40 and channel walls 172 to further assist with retaining collector end 10a within the channel of housing 102.

Circumferential ridge 50 is now disposed between ledges 176 and ridges 177. Plug 40 of collector end 10a is preferably sized so that when disposed between ledges 176 and ridges 177, plug handle end 54 is disposed below opening 166 so that collector end 10a is fully contained within upper extending section 166a when locked to cassette 100. Preferably, a second downward force applied to collector end 10a will displace circumferential ridge 50 past ridge 177, thereby providing a second lock. This second applied force to collector end 10a both locks collector end 10a below ridge 177 and expresses sample into the well area of housing 102.

Although both a ledge 176 and ridge 177 are formed on channel walls 172, only one ridge may be used. The use of both a first and second locking position in channel may be desirable for locking collector 10 to cassette 100 without expression of the sample into well area (when collector end 10a is disposed between ledge 176 and ridge 177), and then later engaging the second lock (when collector end 10a is disposed below ridge 177) when expressing the sample into well area for assay.

The cooperating vertical grooves 174 and ridges 52 are preferably formed on channel walls 172 and plug 40, respectively, to facilitate removal of handle 12 from collector end 10a after collector end 10a has been locked into the channel of housing 102. As discussed earlier, handle 12 is attached to plug 40 by first pressing open end 18 of handle 12 into handle end 54 of plug 40 and then rotating handle 12 relative to plug 40 to engage a locking fit. When removing handle 12 from plug 40, this process is reversed, i.e., handle 12 is lifted from plug 40 and then twisted about plug 40 to disengage the handle-plug lock. When handle 12 is twisted, ridges 52 bear against grooves 174 to prevent rotation of plug 40 as handle 12 is rotated, thereby allowing handle 12 to be easily removed from plug 40.

Although not necessary, it is preferred to form opening 166, upwardly extending section 166a and plug 40 such that a snug fit is achieved between upwardly extending section 166a and plug 40 since this fit deters sample from escaping from opening 166 after expression. Thus, by providing a relatively snug fit between plug 40 and upwardly extending section 166a in addition to the locking feature previously discussed, the preferred embodiment provides a design whereby a collector containing sample can be delivered to the test device and then locked and sealed in the test device. Such a diagnostic tool is highly desirable in the instances where the tool is used, for example, to collect and test for illicit drug use or infectious diseases where there are obvious needs to use a test system that is both tamper resistant and reduces the instances where an administer of the test comes into contact with the sample. If it is desirable to improve the quality of the seal, plug 40 and/or upwardly extending section 166a may further include a fluid sealing member, e.g., a rubber-like member coupled to plug 40 and/or upwardly extending section, such as a gasket.

In the preferred embodiment, a ring 17, formed on handle 12 of collector 10, is used to visually indicate that collector 10 has been fully inserted into cassette 10, that the ampoule has been broken, and that a sample sufficient for assay has been expressed into well portion 108. A raised circumferential ridge formed on handle 12 is preferably used as ring 17, although other types of indicia may be used. FIGS. 9-11 show three sequential positions of collector 10 relative to cassette 100 as collector 10 is inserted into cassette 100 and sample is expressed into well portion 108. FIG. 11 illustrates the position of collector 10 within cassette 100 after a sample has been expressed into well portion 108. When ring 17 is aligned with opening 166, as shown in FIG. 11, collector 10 is fully inserted into cassette 100, thus indicating that the sample collector has been properly inserted, the ampoule broken and the sample has been expressed for assay.

A preferred use for collector 10 and cassette 100 as a diagnostic device will now be discussed, with reference to FIGS. 3-5 and FIGS. 9-11, in the context of a preferred use for the diagnostic device, the collection and assay of saliva from an oral cavity. The diagnostic tool may alternatively be used to collect samples of urine, blood or other fluids. Such other uses can be easily practiced based on the following description.

Collector 10 is used to collect sample. The collection process begins by inserting collector end 10a into the oral cavity. Once positioned within the oral cavity, sponge 90 begins to absorb fluid. As fluid is absorbed, sponge 90 will grow in length. The collector 10 may be periodically removed from the oral cavity to determine whether a sufficient volume of sample has been collected by comparing the length of sponge 90 to length $L_3$, as discussed above. Once sponge 90 has expanded so as to have a length which is approximately equal to length $L_3$, a sufficient volume of sample has been collected from the oral cavity and the sample may now be expressed into cassette 100 for assay.

Referring to FIGS. 8-11, collector end 10a is aligned with and inserted into opening 166 and then pressed into the well area of cassette 100. Expression of the sample and locking of collector end 10a into well portion 108 of cassette 100 is accomplished by forcing collector end 10a into the well portion 108, thereby displacing ridge 50 of plug 40 past ridge 177 formed in channel walls 172. As ridge 50 moves past ridge 177, bump 81 of disc 78 first engages and crushes ampoule 192, thereby discharging a treatment solution. Disc 78 then continues traveling downward until bump 81 reaches the sample receiving portion of assay strip 194, which is supported by lower well wall 132. As bump 81 is engaged with sample receiving portion of assay strip 194, plunger 60 slides within channel 41, thereby expressing sample from sponge 90 into well portion 108. As discussed earlier, the fluid passages formed by extensions 79 and holes 80 allow a portion of sample to flow directly into sample receiving portion of assay strip 194 as sample is expressed from sponge 90, although a significant portion of sample will also escape from sponge 90 by traveling over the sides of disc 78. After collector end 10a has been fully pressed into the sample receiving portion of assay strip 194, wall 74 of second portion 61b of plunger 60 abuts end part 44 of plug 40 (thereby configuring plug 40, plunger 60 and sponge 90 as shown in FIG. 5) and a portion of sample is retained in sponge 90 for confirmatory analysis, if desired. Handle 12 may now be removed from collector end 10a by lifting and twisting handle 12 counter clockwise relative to plug 40 to disengage the handle-plug lock. As sample receiving portion of assay strip 194 becomes wetted with sample and treatment solution, capillary action will begin to draw the sample and solution across the test portion of assay strip 194. Cassette 100 should be held relatively level as sample migrates through the assay strip 194, rather than tipped abruptly forward, to prevent mixed sample and treatment solution from flooding assay portion 182. After allowing a sufficient amount of time for sample flow, the absorbent pad of assay strip 194, viewable through window 186, may be viewed to determine whether the test is completed. Results may now be viewed through window 184, either by the naked eye or by a using instrument, such as a reader.

If desirable, the retained portion of the sample collected on sponge 90 may be removed by separating housing 130 and housing 110 and removing plug 40, plunger 60 and sponge 90 from upper housing 130. The adaptability of cassette 100 for use with other types of sample delivery devices will be apparent based on the detailed description and accompanying claims which follow. Collector 10 is also readily adaptable with collection and/or test devices other than cassette 100, as will also be apparent.

It will be apparent to those skilled in the art that, while the present invention has been disclosed with reference to certain embodiments, numerous modifications, alterations and changes to the described embodiments are possible without departing from the spirit or scope of the present invention, as defined in the appended claims. Accordingly, it is intended that the present invention not be limited to the described embodiments, but that it has the full scope defined by the language of the following claims, and equivalents thereof.

What we claim is:

1. A sample collection device for assay comprising:
   a plunger, including a plunger arm coupled to a disk, where
      the plunger arm includes
      a first diameter portion, and
      a second diameter portion that is larger than the first diameter portion and where the disk is disposed on the second diameter portion; and
      a recess;
   a plug, including
      an end wall and a channel, where the end wall defines an opening holding the recess of the plunger and where the channel is configured for slidably receiving the first diameter portion of the plunger arm into the channel of the plug; and an expandable sponge coaxially disposed on the first diameter portion of the plunger arm, wherein the sample collection device is configured in a sample collection size when the first diameter portion and the second diameter portion of the plunger arm are outside the channel of the plug prior to collecting a sample with the expandable sponge;

an expanded size when the first diameter portion and the second diameter portion of the plunger arm are outside the channel of the plug and the sample was collected with the expandable sponge such that the expandable sponge extends from the end wall of the plug to the disk over the first diameter portion of the plunger arm and the second diameter portion of the plunger arm providing an indication to a user that an adequate sample size was collected; and a sample retaining size when the first diameter portion of the plunger arm is slidably received into the channel of the plug expressing a portion of the sample from the expandable sponge while the second diameter portion of the plunger arm remains outside the channel of the plug retaining a portion of the sample in the expandable sponge.

2. The sample collection device for assay of claim 1, further comprising:

a flange formed on the recess portion of the plunger arm within the channel of the plug and configured to retain the plunger in the plug during sample collection and when the sample is expressed from the sponge.

3. The sample collection device for assay of claim 1, wherein the sample collection device is selectively configurable between the expanded sample collection size and the sample retaining size based upon the length of the second diameter portion of the plunger.

4. The sample collector device for assay of claim 1, wherein sample adequacy is indicated to a user when the length of the sponge in the expanded configuration is substantially equal to the length of the plunger and plug of the sample collection device in the expanded configuration.

5. The sample collector device for assay of claim 3, wherein the sample collection device is further configurable between the expanded sample collection size and the sample retaining size based upon the position of a flange on the recess portion of the plunger arm.

6. The sample collector device for assay of claim 1, wherein the sponge size is reduced from the expanded collection size to the sample retaining size when the sample collection device is reconfigured from the expanded size to the sample retaining size.

7. The sample collector device for assay of claim 6, wherein a first portion of the sample for assay is discharged when the plunger arm is moved relative to the end wall of the plug such that the plunger arm reconfigures the sponge from the expanded size to the smaller sample retaining size and a second portion of sample is retained in the sponge for subsequent assay.

8. The sample collection device for assay of claim 1, wherein when the sample collection device is reconfigured from the expanded collection size to the sample retaining size, the sponge is configured from the expanded collection size to the sample retaining size and a sample sufficient for a first assay is expressed from the sponge.

* * * * *